United States Patent
De Voss

[11] Patent Number: 6,029,658
[45] Date of Patent: Feb. 29, 2000

[54] NASAL DILATOR AND A METHOD OF PRODUCING SAME

[76] Inventor: Torsten De Voss, Engkaer 22, Hvidovre, DK-2650, Denmark

[21] Appl. No.: 08/817,463
[22] PCT Filed: Apr. 16, 1997
[86] PCT No.: PCT/DK97/00164
§ 371 Date: Jun. 12, 1997
§ 102(e) Date: Jun. 12, 1997
[87] PCT Pub. No.: WO97/38651
PCT Pub. Date: Oct. 23, 1997

[30] Foreign Application Priority Data

Apr. 16, 1996 [DK] Denmark ............................. 96 00247
Apr. 16, 1996 [DK] Denmark ............................. 0443/96

[51] Int. Cl.[7] .................................................. A61M 15/00
[52] U.S. Cl. .............................. 128/200.24; 128/207.18; 606/199; 606/204.45
[58] Field of Search ................... 128/200.24, 204.18, 128/207.14, 207.18; 606/199, 204.45

[56] References Cited

U.S. PATENT DOCUMENTS

| | | | |
|---|---|---|---|
| 1,292,083 | 1/1919 | Sawyer | 606/199 |
| 1,950,839 | 3/1934 | Chirila | 606/199 |
| 5,476,091 | 12/1995 | Johnson | 128/200.24 |
| 5,533,499 | 7/1996 | Johnson | 128/200.24 |
| 5,533,503 | 7/1996 | Doubek et al. | 128/200.24 |
| 5,533,605 | 7/1996 | Mays et al. | 194/206 |
| 5,546,929 | 8/1996 | Muchin | 128/200.24 |
| 5,611,333 | 3/1997 | Johnson | 128/200.24 |
| 5,611,334 | 3/1997 | Muchin | 128/200.24 |
| 5,653,224 | 8/1997 | Johnson | 606/199 |
| 5,706,800 | 1/1998 | Cronk et al. | 606/199 |
| 5,718,224 | 2/1998 | Muchin | 606/199 |
| 5,890,486 | 4/1999 | Mitra et al. | 606/199 |
| 5,931,854 | 8/1999 | Dillon | 606/199 |

FOREIGN PATENT DOCUMENTS

92/22340 12/1992 WIPO.
94/23675 10/1994 WIPO.

OTHER PUBLICATIONS

"Breathe Right" ® article, CNS., Inc., Chanhassen, MN 55317. 1–800–843–2978. Article #6100–643–001 6100–607–001. 1994.

*Primary Examiner*—Aaron J. Lewis

[57] ABSTRACT

A nasal dilator (10") for placing on a user's nose and for improving respiration through the nose by dilation of the user's nostrils comprises a central, resilient, beam-shaped element (12) and two attaching elements (14 and 16) placed at respective ends of the beam-shaped element for attachment to respective sides of the user's nose. The beam-shaped element (12) extends in use from one side of the user's nose across the bridge of the user's nose to the other side of the user's nose and the central, resilient, beam-shaped element (12) and the two attaching elements (14, 16) are integrally made of plastic. The nasal dilator (10") constitutes a configuration which is symmetrical relative to a central plane perpendicular to the longitudinal axis of the beam-shaped element and preferably constitutes an overall curved structure or alternatively a substantially plane structure. The central, resilient, beam-shaped element exhibits a rigidity increasing from the central plane towards the two attaching elements (14, 16) and the two attaching elements constitute substantially, plane, flat-shaped elements constituting extensions of the central, resilient, beam-shaped element (12) to which attaching elements a skin-compatible adhesive (20) is applied.

17 Claims, 3 Drawing Sheets

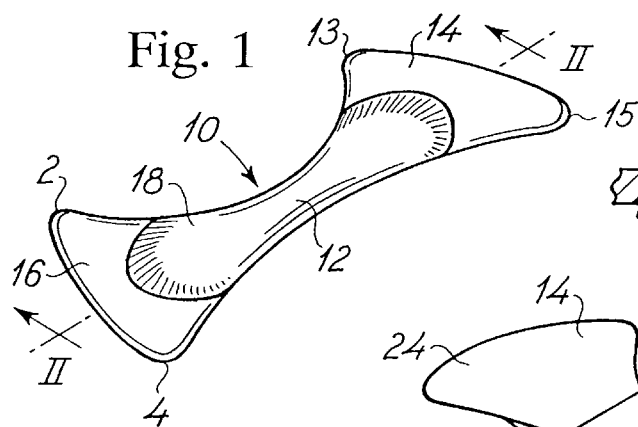
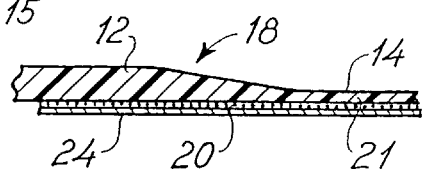
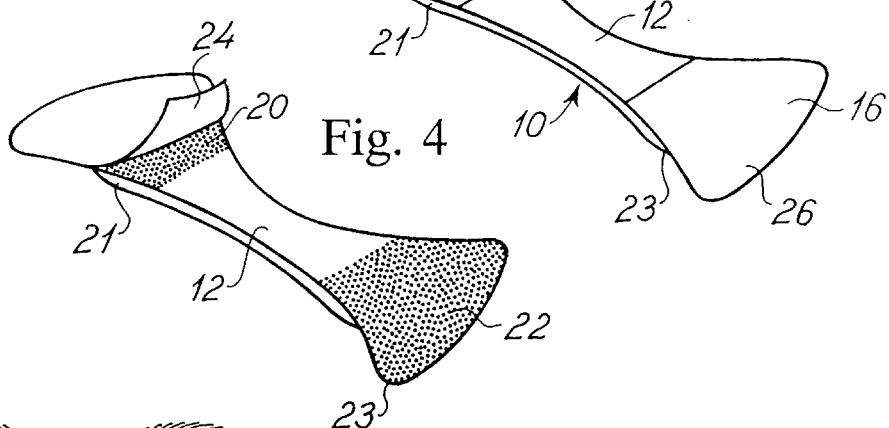
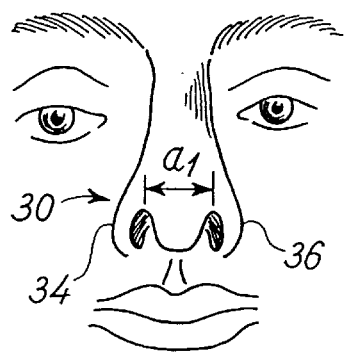
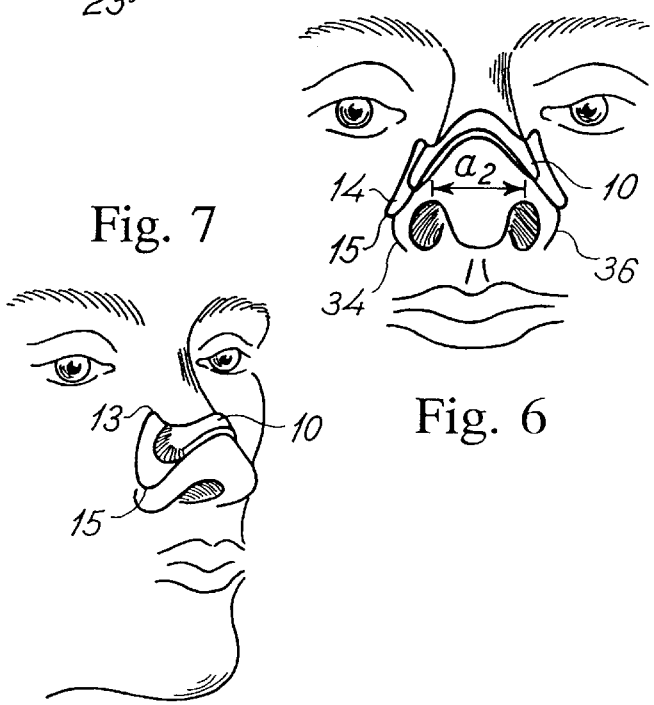

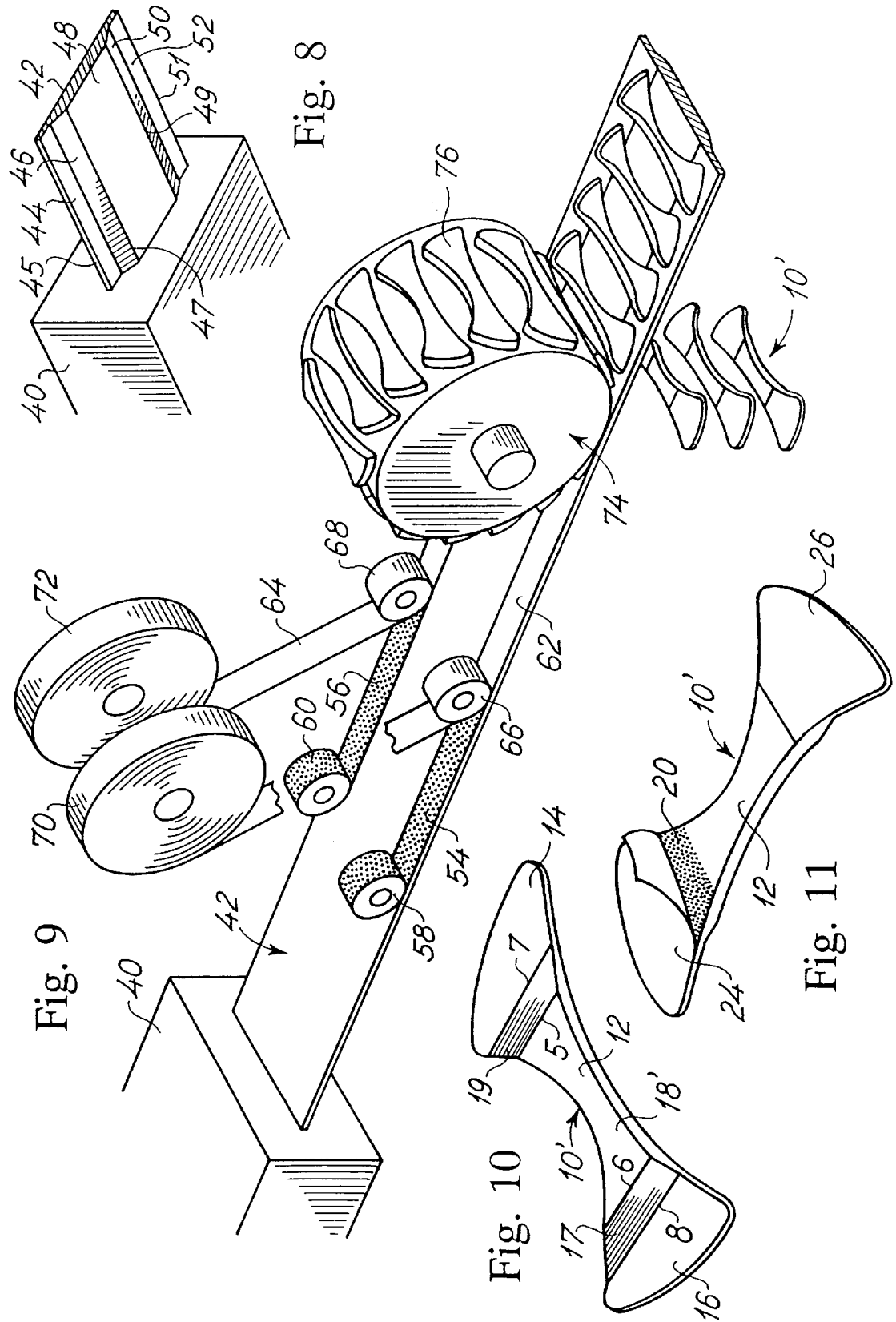

NASAL DILATOR AND A METHOD OF PRODUCING SAME

BACKGROUND OF THE INVENTION

1. Field of the Invention

The present invention relates to a nasal dilator for placing on the nose of a user for improving the breathing through the user's nose by dilating the user's nostrils. The nasal dilator generally comprises a central, resilient, beam-shaped element and two attaching elements placed at respective ends of the beam-shaped element and adapted in use to be attached to respective sides of the user's nose, as the beam-shaped element in use extends from one side of the user's nose over the bridge of the nose to the other side of the user's nose.

A nasal dilator of the above described type is designed for people who suffer from difficulties in breathing caused by malformations of the nostril passages, illnesses such as polyps, allergies such as hayfever, and who often have to breathe through the mouth, which may lead to irritation of the lungs, anxiety, sleeping problems and snorring, and for people practicing sport and thus having to inhale a larger air volume than the usual one.

2. Description of the Prior Art

A nasal dilator of the above described type is known from U.S. Pat. No. 1,292,083 which describes a construction which, according to the inventor, is designed for use by persons suffering from breathing problems, especially hayfever, and who, by using the nasal dilator, can breathe a larger air volume through the nose. The construction consists of three components, i.e. two attaching elements formed as adhesive cushions or suction cups and designed for being attached on each side of the user's nose, and a central beam-shaped, flexible element exerting tension on the attaching elements, thus keeping the nostrils in a dilated or expanded state.

Similar nasal dilators are disclosed in the international patent applications WO 92/22340 and WO 94/23675 and in U.S. Pat. No. 5,476,091, U.S. Pat. No. 5,533,499, and U.S. Pat. No. 5,533,503 to which reference is made and which are hereby incorporated in the present specification by reference. Additional dilator devices are disclosed in U.S. Pat. No. 5,546,929 and U.S. Pat. No. 5,553,605 (Acutek) to which reference is made and which are hereby incorporated in the present specification by reference. These dilators, however, all suffer from the drawback that they are of a complex construction.

Published international application WO 92/22340 discloses a nasal dilator consisting of a central band of flexible material having an adhesive coating applied to one side thereof, the adhesive being shaped with opposite end elements and an intermediary connecting segment. An absorbing cushion is mounted on the upper side of the segment, on the adhesive coating, for absorption of moisture or perspiration when the construction is mounted on the user's nose with the cushion facing the bridge of the nose with the adhesive-coated end elements fixated to the sides of the user's nose. The construction constitutes in its entirety a conventional plaster per se having attached release paper on the exterior, adhesive side thereof in the conventional manner. On the opposite or other side of the band, i.e. the side opposite the adhesive coating, the construction is provided with resilient bands attached to the other side of the band by means of respective adhesive elements which are shaped as a double adhesive tape.

Published international patent application WO94/23675 discloses a nasal dilator which per se can be regarded as a development of the nasal dilator disclosed in the above-mentioned older international patent application. The modified or improved nasal dilator provides a sandwich construction comprising a further (in relation to the prior construction) foil which eliminates the sensation of inconvenience and irritation due to the cutting and peeling forces which appear when using the model according to WO92/22340. The adhesive, which in both the above-mentioned older patent applications is used for applying the nasal dilator onto the skin, is preferably biocompatible and diffusion-open.

The above-mentioned nasal dilators have the common characteristic that, containing several individual components, they show limitations relative to the complicated configuration, and that the diffusion-open adhesive allows perspiration, moisture or sebum to penetrate through the adhesive area and the adhesive band, reducing the effectivity of the adhesion and, consequently, the adhesion area, which in turn leads to loosening of the nasal dilator and the final detachment thereof.

SUMMARY OF THE INVENTION

One object of the present invention is to provide an extremely simple nasal dilator designed to be placed on the nose of a user for improving his or her breathing through the nose by dilating the user's nostrils, which nasal dilator ensures a durable and firm adhesion also during physical effort and which dilator at the same time retains all the advantageous characteristics of the prior art dilators or even improves them.

An advantage of the nasal dilator according to the present invention is that the attaching elements can be formed in a particular shape adapted to a better positioning of the attaching elements to the nose wings, thus ensuring better adhesion to the nose wings and a larger adhesive area.

Another advantage of the nasal dilator according to the present invention is that the particular configuration of the nasal dilator ensures good transfer and distribution of the tensile and shearing forces on the wide attaching elements and thus durable and firm adhesion.

A further advantage of the nasal dilator according to the present invention is that the nasal dilator can be made of UV-transparent material and thus allow the user to get a tan even when using the nasal dilator.

Furthermore, the use of a special diffusion-tight adhesive ensures that the novel nasal dilator does not loosen and detach during a longer period of use.

The above objects and advantages are achieved by a nasal dilator according the present invention, comprising a central, resilient, beam-shaped element and two attaching elements placed at respective ends of said beam-shaped element for attachment to respective sides of the user's nose, said beam-shaped element extending in use from one side of the user's nose across the bridge of the user's nose to the other side of the user's nose, said central, resilient, beam-shaped element and said two attaching elements being integrally made of plastic, said nasal dilator constituting a construction which is symmetrical relative to a central plane perpendicular to the longitudinal axis of said beam-shaped element, said central, resilient, beam-shaped element exhibiting a rigidity increasing from said central plane towards said two attaching elements, and said two attaching elements constituting substantially plane, flat-shaped elements constituting extensions of said central, resilient, beam-shaped element, and said two attaching elements being covered by a skin-compatible adhesive.

The nasal dilator, which is symmetrical, is made in one piece from a suitable resilient material, such as different types of plastic, e.g. polyethylene or polypropylene, and comprises a central, resilient, beam-shaped element which has a bending rigidity that is symmetrically increasing from the center towards the ends thereof, and two broad attaching ends or elements constituting essentially plane extensions of the central, resilient, beam-shaped element having applied on one of their sides a skin-compatible adhesive. The nasal dilator is placed on a user's nose so that the attaching ends are attached to the nostrils by means of the adhesive and the form of the ends ensures good adhesion to the nostril skin. The central section is bent and placed as a saddle over the bridge of the user's nose, which creates a tension in the nasal dilator, and the resilience of the material renders it possible for the two ends to pull the nostrils in opposite directions trying to regain their untensed position, thus creating a larger space between the nostrils and the central nasal cartilage, a larger nostril section and, subsequently, improved breathing. The bending of the central section produces at the attaching sites forces similar to those appearing when fixing beams, i.e. normal (tensile) and tangential (shearing) forces, and the broad ends ensure that the forces produced inside the nasal dilator are distributed over a larger area so that they are counterbalanced by the adhesive forces.

In the preferred embodiment of the nasal dilator according to the present invention, the increasing rigidity from the center towards the ends of the beam-shaped element is achieved by the beam-shaped element having a central narrowing and widening towards the two attaching elements. The thickness of the beam-shaped element is in the same preferred embodiment considerably larger than the thickness of the attaching elements, typically approx. 4 times, and the transition from the elevated, central element to the flat end elements is achieved by a very small inclination providing a very even distribution of the tensile and shearing forces produced by tension when placing the beam-shaped element on the nose.

In another preferred embodiment of the nasal dilator according to the present invention, the increasing rigidity from the center towards the ends of the beam-shaped element is achieved by a variation in the density of the beam-shaped element, increasing from the center towards the ends, which variation in density can be achieved by different injection moulding methods through laminating layers of different densities together or through similar techniques. In a further preferred embodiment, the variation in the density of the beam-shaped form is achieved by providing weakening grooves along the central beam.

For achieving a larger adhesive area and for providing an improved adaptation of the shape of the end regions to the shape and curvature of the nose wings, the attaching elements in the preferred embodiment have the configuration of a butterfly wing, but they may also be triangular, rectangular, round, oval, or they may have any other geometrical form following the curved shape of the nose wings so as to ensure the largest possible adhesive area to avoid that the user feels uncomfortable.

In accordance with alternative embodiments, the nasal dilator according to the present invention may in a first embodiment constitute a substantially planar structure and in another, presently preferred embodiment constitute a substantially curved structure defining an initially convex structure to be applied straddling the nose of the user. Alternatively, the curved structure may constitute a convex structure producing an increased flexibility as compared to a planar structure or a curved structure constituting a convex structure. By providing the nasal dilator according to the present invention constituting a substantially curved, convex structure, the user readily perceives the correct and intentional orientation of the nasal dilator before applying the nasal dilator to the user's nose.

In a preferred embodiment of the nasal dilator according to the present invention, the attachment of the nasal dilator to the nostrils is ensured by a skin-compatible, diffusion-tight adhesive which doesn't allow sweat, moisture or sebum to penetrate through the adhesive coating and weaken the adhesion forces between the skin and the adhesive.

In another preferred embodiment of the nasal dilator according to the present invention, the skin-compatible adhesive is diffusion-open. In a further preferred embodiment the nasal dilator is attached to the nose by means of double adhesive tape covered by a non-adhesive release paper.

Alternative materials which fulfil the required resilience demands and which may be used in the production of nasal dilators are plastic materials, such as polyethylene, polypropylene, polyvinylchloride, or similar soft plastic materials or mixtures thereof.

The nasal dilator according to the present invention can be produced in several manners:

a) injection moulding in one piece, followed by adhering adhesive to the attaching elements, and b) continuous or intermittent punching or stamping of a previously laminated and profiled plastic band having a profile providing the desired, increasing rigidity from the center of the beam section to the ends thereof, and on the smooth part of which an adhesive tape is adhered before stamping or punching.

BRIEF DESCRIPTION OF THE DRAWINGS

The invention will now be described with reference to the drawings on which:

FIG. 1 is a perspective view of a preferred embodiment of the dilator according to the present invention, FIG. 2 is a fragmentary cross-sectional view along the line II—II of FIG. 1, showing an adhesive tape attached to one side of the nasal dilator and covered by release paper, FIG. 3 is a perspective view disclosing the adhesive area covered by release paper seen from the skin-contacting side of the nasal dilator of FIGS. 1 and 2, FIG. 4 is a perspective view of the adhesive area, seen from the skin-contacting side of the nasal dilator of FIGS. 1, 2 and 3, FIG. 5 is a schematic front view of a user with the nostrils in a normal, undilated state, FIG. 6 is a schematic front view of a user having the nasal dilator of FIG. 1 attached to the nose with the nostrils in a dilated state, FIG. 7 is a schematic, perspective semiprofile view of a user having the nasal dilator of FIGS. 1–4 according to the invention attached to the nose, FIG. 8 is a perspective view disclosing an extruded plastic bar having the desired profile, with a plane side and an elevated side, FIG. 9 is a schematic, perspective view of a preferred process of producing a nasal dilator according to the present invention, FIG. 10 is a perspective view of an alternative embodiment of the nasal dilator seen from the elevated side and produced by punching or stamping of a profiled plastic band, FIG. 11 is a perspective view of the adhesive area of the nasal dilator of FIG. 10, covered by release foil and seen from the skin-contacting side.

DETAILED DESCRIPTION OF THE PREFERRED EMBODIMENT

Figure 12:
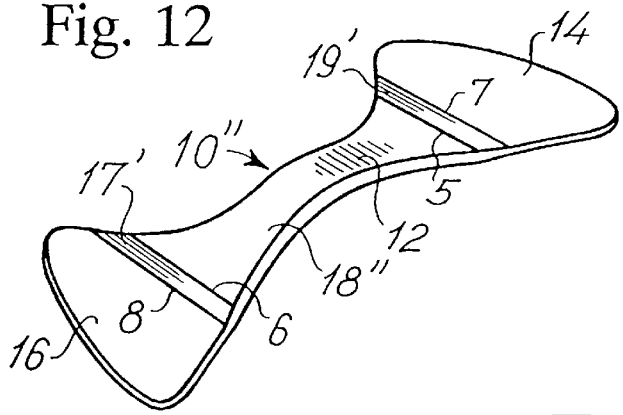
FIG. 12 is a perspective view similar to the view of FIG. 10 of a further alternative embodiment of the nasal dilator constituting a substantially curved structure seen from the elevated side.

In the present context, terms such as upper, lower, inner, outer, convex, concave, etc. refer, unless otherwise defined, to the intentional orientation of a nasal dilator to be applied and fixated straddling the nose of a user. In the following description, primed reference numerals correspond to identical or similar parts.

FIG. 1 is a perspective view of a side or an elevated side of a nasal dilator 10 according to the present invention. The dilator according to the present invention is seen to have a shape resembling a butterfly, with a long central, resilient, beam-shaped element 12 and two wing-like ends 14, 16 for attachment to a user's nose. The nasal dilator is symmetrical relative to a plane perpendicular to the longitudinal axis of the beam-shaped element and not symmetrical relative to a longitudinal plane with respect to the beam-like element. The dilator is shaped in such a manner that the central, beam-shaped region 12 is elevated on one side, and consequently thicker than the regions 14, 16 at the wing-like ends, which can better be seen in FIG. 2. From a geometrical point of view, the shape of the nasal dilator may be described as the non-superposed part of a first circle intersecting two closely neighbouring circles which are coaxial with the first circle and do not intersect each other, one having a radius being substantially equal to the radius of the first circle, the other having a radius substantially larger, the angles resulting from the intersection being rounded.

In FIG. 2, a cross-section along the axis II—II of FIG. 1 is shown, disclosing that that the nasal dilator 10 has a smooth or a plane side 11, which is the side facing or contacting the skin of the user's nose, and another side 18 being elevated in the central, beam-shaped element 12, and that the transition between the central, elevated part and the margins of the attachment element is gradual, with a very low inclination. The large area of the margins 14 and 16, their particular shape comprising unequal wing tips 13, 15 and 2, 4, respectively, of which the most prominent, 15 and 4, respectively, in use face downwards toward the bridge of the nose, their relative thinness and consequently their higher flexibility and capacity to adapt to the shape of the wings of the nose 34 and 36, and the slight inclination between the elevated part 12 and the thinner parts 14 and 16 ensure good transfer and distribution of the tensile and shearing forces appearing when bending the dilator and attaching it to the nose.

In FIG. 2, an adhesive coating 20 is shown applied to the plane side 21 of the wing region 14 and covered by a release paper 24, i.e. before the dilator is attached to the nose. The figure shows the ratio between the thickness of the elevated region 18 and the thickness of the thin layer 14. In practice, the thickness of the elevated region 18 is approx. 1.2–1.5 mm, typically 1.3–1.35 mm, and the thickness of the attachment elements 14 and 16 is approx. 0.3 mm, the thickness ratio being of the order of magnitude of 4–5.

FIG. 3 is a perspective view of the nasal dilator 10 according to the invention, seen from the skin-contacting side or the plane side 11 which are covered at their outermost or broad ends on the plane end regions 21, 23 by the adhesive coatings 20, 22 which are further covered by pieces of non-adhesive foil or release paper 24, 26, respectively. The extent of the adhesive coatings on the plane side can be seen in the figure.

FIG. 4 is a perspective view corresponding to the view of FIG. 3, showing the nasal dilator 10 according to the invention, seen from the skin-contacting side or the plane side 11, with the non-adhesive foil 24 removed from one end and slightly lifted from the other side. The removed foil reveals the adhesive coating 22, 20 on the attachment ends. In this embodiment, a skin-friendly, non-aggressive, diffusion-tight adhesive is preferably used, allowing athletes, in particular, to carry the nasal dilator according to the invention without the dilator losing its adhesive properties due to moisture or sebum.

FIG. 5 is a schematical front view of a user 30 having the nostrils 34, 36 in a normal, non-dilated state defined by the distance $a_1$, between the nostrils, without the application of the nasal dilator 10.

FIG. 6 is a schematical front view of the user with a nasal dilator 10 for improving breathing through the nose by dilating the user's nostrils 34, 36. It appears from the figure that the use of the nasal dilator 10 leads to a larger distance between the nostrils $a_2>a_1$. A clearer view of the placement of the dilator on the nose is given in FIG. 7 where it can be seen that the most prominent tip 15 of the wing area 14 in use points downwards towards the bridge of the nose and follows the curvature of the wing of the nose, ensuring a larger adhesive area and better adhesion between the plane attaching element 21 and the wing of the nose 34.

FIG. 8 shows a plastic bar 42 seen from its elevated side and showing the desired profile according to one of the alternative embodiments of the invention, i.e. a smooth side and an elevated side with sharp separation lines between the respective areas. The plastic bar 42 is extruded by means of an extrusion tool 40 and has a central, elevated part 48, two inclined transitional regions 46 and 50, and two marginal regions 44 and 52. The central part 48 is separated from the transitional regions 46 and 50 by separation lines 47 and 49, respectively, and the marginal regions 44 and 52 are separated from the transitional regions 46 and 50 by separation lines 45 and 51, respectively.

FIG. 9 is a schematical, perspective view of a preferred method of producing a nasal dilator according to the present invention. A rotary punching tool 74 is shown with protruding punching profiles 76 matching perfectly the shape of the nasal dilator 10, an extruded plastic bar 42 produced by means of the extrusion tool 40, two double adhesive tapes 54, 56 originating from two adhesive tape rolls 58, 60, two respective paper bands 62, 64 with the same breadth as the adhesive tape rolls 58, 60 and originating from two paper band rolls 70, 72, and two respective rolls 60, 68. To produce the nasal dilator 10' the adhesive tape rolls 58, 60 are rolled on the plane side 11' along the margins of the plastic bar 42, and on top of them the paper band rolls 70, 72 are rolled by means of the rolls 60 and 68 which press the paper band rolls 70, 72 against the plane side of the plastic bar 42 so that the paper band rolls 70, 72 perfectly overlap the adhesive coating on the plane side 10'. The rotary punching tool 74 is thereafter rolled along the length of the plane side 10' and its profiles cut out in the plastic bar 48 the nasal dilators 10' in their finished shape, with double adhesive tape adhered to the plane side 11' and covered by paper foil.

FIG. 10 is a perspective view of a nasal dilator 10' according to the present invention, produced by punching a profiled plastic band 42. FIG. 10 shows that the transitional region between the central part 18' and the end parts 14 and 16 is plane, and that the connection between the plane transitional region 19 and the central part 12 and the end part 14, respectively, is not rounded, but forms straight separation lines 5 and 7, respectively. The same applies for the symmetrical half of the nasal dilator, where the separation lines between the plane transitional area 17 and the the central part 12 and the end part 16, respectively, forms sharp separation lines 6 and 8, respectively.

FIG. 11 is a perspective view of the nasal dilator of FIG. 10 seen from the skin-contacting side, i.e. the plane side 19, having applied on the adhesive coatings 20 and 22 the release paper foils 24 and 26, respectively. The release paper foil 26 entirely covers the adhesive coating 22, whereas the release paper foil 24 is shown slightly lifted, allowing visual inspection of the adhesive coating 20.

FIG. 12 is a perspective view similar to the view of FIG. 10 of a nasal dilator 10" according to the present invention also produced by punching a profiled plastic band 42 as illustrated in FIG. 9. The nasal dilator 10" basically constitutes a structure similar to the structure of FIG. 10, however, differing from the structure of FIG. 10 in that the nasal dilator of FIG. 12 is a generally curved structure, whereas the nasal dilator of FIG. 10 is a generally plane structure. The end parts 14 and 16 of the nasal dilator 10" are interconnected through the central part 18" which is curved as compared to the substantially planar central part 18' of the nasal dilator 10' illustrated in FIG. 10. The nasal dilator 10" further differs from the nasal dilator 10' illustrated in FIG. 10 in that the plane transition areas 17' and 18' delimited between the straight separation lines 6,8 and 5,7, respectively, are somewhat narrower as compared to the transition areas 17 and 19, respectively, illustrated in FIG. 10.

Figure 13:
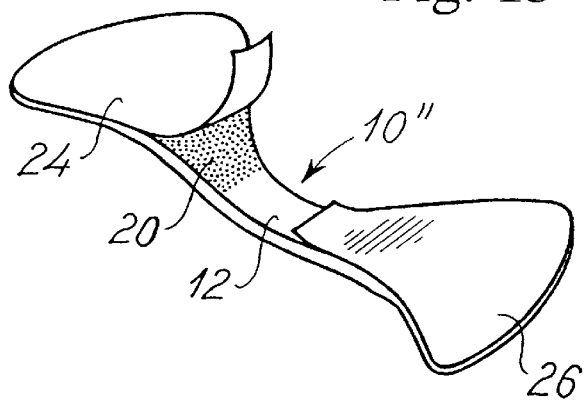
FIG. 13 is a perspective view similar to the view of FIG. 11 of the adhesive area of the nasal dilator of FIG. 12, and FIGS. 14 and 15 are perspective views similar to the view of FIG. 12 of a further modified embodiment of the nasal dilator as compared to the embodiment of FIG. 12 illustrating the nasal dilator in two different states.

FIG. 13 is a perspective view of the nasal dilator of FIG. 12 seen from the skin-contacting side, i.e. the lower curved side. In FIG. 13, the adhesive coating 20 is partly exposed, whereas the adhesive coating 22 is covered by the release paper foil 26.

Figure 14:
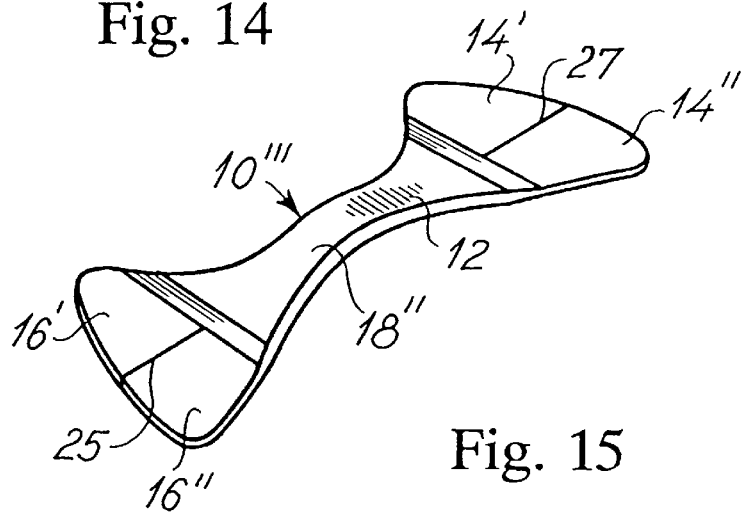
Figure 15:
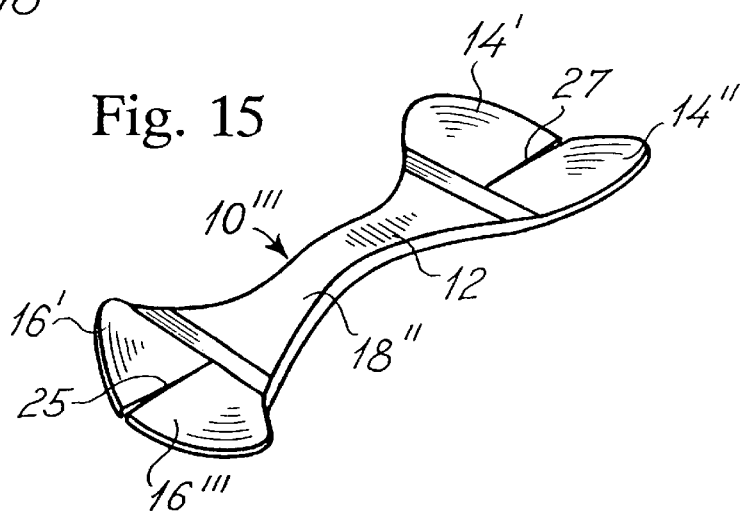

FIGS. 14 and 15 are perspective views similar to the view of FIG. 12 illustrating a further modified embodiment of the nasal dilator according to the present invention as compared to the nasal dilator 10' illustrated in FIG. 12. The further modified nasal dilator illustrated in FIGS. 14 and 15 is designated the reference numeral 10'" and differs from the above described embodiment 10" in that the end parts 14 and 16 of the dilator 10" are cut into two parts 14', 14" and 16', 16", respectively, through separation lines or cuts 27 and 25, respectively. By separating the end parts 14 and 16 of the dilator 10" illustrated in FIG. 12 into segmented end parts 14', 14" and 16', 16", respectively, the end parts of the overall structure are allowed to flex and adopt a configuration as illustrated in FIG. 15, allowing the end parts of the dilator 10'" to readily conform to the configuration of the nose of the user as the outer contour of the nose of the user seldom constitutes two opposite plane surfaces but more often defines bends or cracks on the side surfaces of the nose to which bend the nasal dilator 10'" readily adopts its shape through the provision of cuts or slits 25 and 27.

The nasal dilator can be produced in several different dimensions and it presents certain ratios between the dimensions thereof; the dilator has in its largest version a maximum length (L) of between 50 and 75 mm, preferably 60 mm, a maximum breadth (B) of between 16 and 25 mm, preferably 20 mm, and the breadth of the central narrowing (b) is between 4 and 6 mm, preferably 5 mm. Thus, the following dimensional ratios in relation to the preferred embodiment are achieved: $L/B=60/20=3$, $L/B=60/5=12$. The dilator is provided in a cross-section along its longer axis with a thickness of the elevated part (T) of 1.3–1.35 mm and a thickness of the flat end part (t) of approx. 0.3 mm. In the smallest version, designed for children, the ratios between the maximum length, the maximum breadth and the breadth of the central narrowing are retained so that the maximum length L is between 40 and 55 mm, preferably 48 mm, the maximum breadth B between 13 and 18 mm, preferably 16 mm, and the breadth of the central narrowing b between 3 and 5 mm, preferably 4 mm, i.e. $L/B=48/16=3$, $L/b=48/4=12$.

The nasal dilator according to the present invention is preferably made from plastic material, such as polyethylene, polypropylene, polyvinylchloride or similar plastic materials or mixtures thereof. The presently preferred embodiments of the nasal dilator according to the present invention as illustrated in FIGS. 10, 11, 12, 13, 14 and 15 are preferably made from low-density polyethylene, such as LDPE of the type NCPE 6600 supplied by the company Borealis Polymers Oy, Finland, or the type LE 6600 supplied by the same company. The adhesive coating applied to the lower side of the nasal dilator may constitute any skin-compatible adhesive, such as a medical grade adhesive generally used within the field of bandages, plaster structures, etc. The adhesive coating may be applied directly to the end parts 14, 16 or may alternatively be presented through a double adhesive tape applied to the end parts 14, 16. Examples of relevant double adhesive tape are tesa 4962™ supplied by the company Beiersdorf A/S, Denmark or Fixomull® stretch tape supplied by the same company. An alternative example of an adhesive material is an adhesive which allows the nasal dilator to be removed from its position straddling the nose of the user and to be repositioned on the nose without ruining the adhesive material and deteriorating the fixture of the nasal dilator as compared to the first or original fixation of the nasal dilator on the nose of the user.

What is claimed is:

1. A nasal dilator for placing on a user's nose and for improving respiration through the nose by dilation of the user's nostrils, said nasal dilator comprising:

a central, resilient, beam-shaped element and two attaching elements placed at respective ends of said beam-shaped element for attachment to respective sides of the user's nose, said beam-shaped element extending in use from one side of the user's nose across the bridge of the user's nose to the other side of the user's nose, said central, resilient, beam-shaped element and said two attaching elements being integrally made of plastic, said nasal dilator constituting a construction which is symmetrical relative to a central plane perpendicular to the longitudinal axis of said beam-shaped element, said central, resilient, beam-shaped element exhibiting a rigidity increasing from said central plane towards said two attaching elements, and said two attaching elements constituting substantially planar, flat shaped elements constituting extensions of said central, resilient, beam-shaped element, and said two attaching elements being covered by a skin-compatible adhesive.

2. A nasal dilator according to claim 1, wherein said nasal dilator defines a planar side.

3. A nasal dilator according to claim 2, wherein said skin-compatible adhesive is applied directly to said planar side.

4. A nasal dilator according to claim 1, wherein said central, resilient, beam-shaped element is elevated relative to said two attaching elements.

5. A nasal dilator according to claim 4, wherein said elevated central, resilient, beam-shaped element is further elevated at the ends thereof.

6. A nasal dilator according to claim 4, wherein said elevated central, resilient, beam-shaped element is thinner in the central region thereof.

7. A nasal dilator according to claim 1, wherein said central, resilient, beam-shaped element has a central narrowing and expanding towards the two attaching elements.

8. A nasal dilator according to claim 7, wherein said attaching elements are butterfly wing-shaped, or triangular, rectangular, oval or round, or of any other suitable geometrical form.

9. A nasal dilator according to claim 1, wherein said central, resilient, beam-shaped element defines a substantially planar structure.

10. A nasal dilator according to claim 1, wherein said central, resilient, beam-shaped element defines a substantially curved structure.

11. A nasal dilator according to claim 1, wherein the density of said central, resilient, beam-shaped clement increases from the center towards the ends thereof for increasing the rigidity from the central plane towards said two attaching elements.

12. A nasal dilator according to claim 1, further comprising weakening grooves provided along said central, resilient, beam-shaped element for increasing the rigidity from the central plane towards the two attaching elements.

13. A nasal dilator according to claim 1, wherein said skin-compatible adhesive is applied to either side of the user's nose by means of a double adhesive tape.

14. A nasal dilator according to claim 1, wherein said skin-compatible adhesive is non-diffusive.

15. A nasal dilator according to claim 1, wherein said skin-compatible adhesive is diffusive.

16. A nasal dilator according to claim 1, wherein said plastic material is polyethylene, polypropylene, polyvinylchloride or a similar soft plastic material, or a mixture thereof.

17. A nasal dilator according to claim 1, wherein the maximum length of said nasal dilator is substantially three times larger than the maximum breadth of said nasal dilator and 12 times larger than the breadth of its narrowed part, and preferably has a maximum length of 60 mm, a maximum breadth of 20 mm, and a breadth of the narrowed part of 5 mm.

* * * * *